United States Patent [19]

Hornstra et al.

[11] Patent Number: 4,649,557
[45] Date of Patent: Mar. 10, 1987

[54] X-RAY ANALYSIS APPARATUS INCLUDING A MONOCHROMATOR CRYSTAL HAVING CRYSTAL LATTICE SURFACES

[75] Inventors: Jan Hornstra; Mathias P. A. Viegers, both of Eindhoven, Netherlands

[73] Assignee: U.S. Philips Corporation, New York, N.Y.

[21] Appl. No.: 623,598

[22] Filed: Jun. 22, 1984

[30] Foreign Application Priority Data

Jun. 27, 1983 [NL] Netherlands ............. 8302263

[51] Int. Cl.[4] ............................................. H03D 3/22
[52] U.S. Cl. ........................................ 378/84; 378/85
[58] Field of Search ............... 378/70, 71, 82, 83–85

[56] References Cited

U.S. PATENT DOCUMENTS

| 2,853,617 | 9/1958 | Berreman | 378/84 |
|---|---|---|---|
| 3,439,163 | 4/1969 | De Jongh | 378/84 |
| 3,639,759 | 2/1972 | Goshi et al. | 378/85 |
| 4,078,175 | 3/1978 | Fletcher et al. | 378/79 |
| 4,203,034 | 5/1980 | Carroll, Jr. | 378/85 |
| 4,322,618 | 3/1982 | Jenkins | 378/84 |
| 4,461,018 | 7/1984 | Ice et al. | 378/84 |

Primary Examiner—Janice A. Howell
Attorney, Agent, or Firm—Paul R. Miller

[57] ABSTRACT

A monochromator in an X-ray analysis apparatus involves a crystal having spherically curved crystal lattice surfaces with the boundary surface of the crystal having a radius of curvature R in a first principal direction and a radius of curvature 2R in a second principal direction. The second principal direction is transverse with respect to the first principal direction. A high radiation efficiency is obtained by constructing an entrance slit and an exit slit for X-rays to conform to curved circles of latitude on a Rowland sphere applicable to the monochromator crystal.

14 Claims, 1 Drawing Figure

U.S. Patent  Mar. 10, 1987  4,649,557
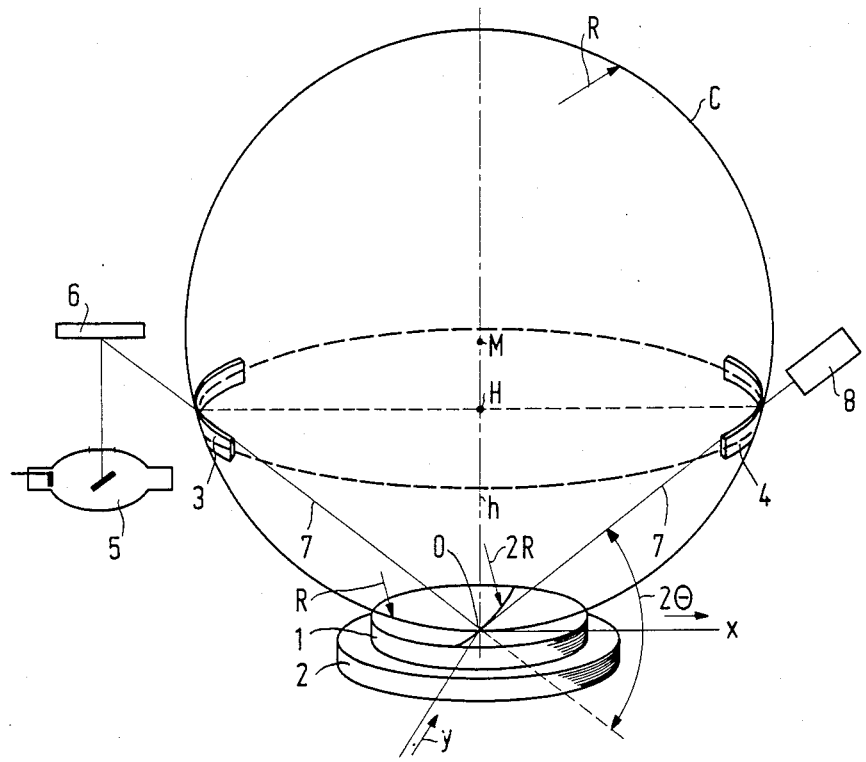

X-RAY ANALYSIS APPARATUS INCLUDING A MONOCHROMATOR CRYSTAL HAVING CRYSTAL LATTICE SURFACES

The invention relates to an X-ray analysis apparatus, comprising an X-ray source, a curved monochromator crystal, and an X-ray detector, and also relates to a method of manufacturing a monochromator crystal for such an X-ray analysis apparatus.

Two types of radiation monochromator arrangements are used in X-ray fluorescence spectrometry. According to a first method, a single wavelength is selected from the polychromatic radiation from a specimen by means of, for example, a logarithmically curved monochromator cryatal in combination with a straight entrance and exit slit. An apparatus of this kind is described in U.S. Pat. No. 3,439,163; this apparatus has a reasonable resolution and a reasonably high radiation efficiency but cannot be used for significantly different wavelengths, i.e. for other elements, and the background in the measurement signals is comparatively high because the radiation slits must be comparatively wide. A second arrangement utilizes an X-ray beam which is not monochromatic, i.e. radiation which spans a wider band of wavelengths. Use is customarily made of a flat crystal in combination with a collimator comprising, for example so-called Soller slits. The resolution is then comparatively low, but the radiation efficiency may be comparatively high. The resolution of such an apparatus can be enhanced by using several monochromator crystals arranged in cascade as disclosed in U.S. Pat. No. 3,639,759. However, this increased resolution occurs at the expense of the radiation efficiency and restricts the ability of the apparatus to be adapted to other wavelengths.

Instead of a logarithmically curved crystal or a flat crystal in combination with Soller slits, use can be made of a monochromator according to Johann which is characterized by a cylindrically curved monocrystal whose reflective crystal lattice surfaces are also cylindrically curved with the same radius of curvature, or of a monochromator according to Johansson in which the crystal is also cylindrically curved but, in order to achieve a focusing effect, the boundary surface is recessed on the concave side of the crystal lattice surfaces so that the (mean) radius of curvature of the crystal lattice surfaces is twice as large as the radius of curvature of the crystal boundary surface in that region. By comparison with the Johann monochromator, a higher resolution is thus obtained, so that narrower slits can be used; and this benefits the signal-to-noise ratio in the measurement signals. In an apparatus embodying a Johansson crystal, wavelength scanning can be performed, provided that the positions of the entrance slit and the crystal can be correctly varied. However, the entrance slits is correctly focused on the exit slit via the monochromator crystal only for radiation which extends perpendicularly to the cylinder axis of the monochromator crystal. Therefore, in order to avoid faults due to focusing errors, it is necessary to sue comparatively short slits and a comparatively narrow crystal.

An example of an X-ray analysis apparatus comprising a monochromator crystal whose crystal lattice surfaces are curved in two directions, is disclosed in U.S. Pat. No. 2,853,617. To achieve this, the crystal is cut in the form of a cylindrical shell-portion or plate having a radius R1, from a monocrystal whose crystal lattice planes (surfaces) extend parallel to two principal end faces. The cylindrical crystal shell thus obtained is subsequently deformed so that it is made flat, thus forming a flat crystal in which the crystal lattice surfaces are cylindrically curved. Subsequently, this crystal is deformed into a cylindrical shape having a cylinder axis directed transversely with respect to the cylinder axis of the crystal lattice surfaces, and having a radius of curvature $R2 = -R1\sin^2 \theta$, $\theta$ being the desired Bragg angle. Viewed in a plane 6—6 as indicated in FIG. 5 of this patent specification, no point-to-point image is obtained. This is because the crystal boundary surface is flat in that cross-section; for focusing according to Johansson it should exhibit a curvature having a radius of curvature which is half that of the respective crystal lattice surfaces. The arrangement described therein is notably not suitable for X-ray fluorescence measurements which require that a specimen should be irradiated over a comparatively large irradiation field.

It is an object of the invention to provide an X-ray analysis apparatus in which a high radiation efficiency is combined with such slit-to-slit imaging that a high resolution can be achieved. For this purpose, an X-ray analysis apparatus of the kind set forth is characterized in that the monochromator crystal comprises doubly curved crystal lattice surfaces, the boundary surface of the crystal, which is to be irradiated, exhibiting mutually different significant amounts of surface curvature in different principal directions.

When such a crystal is used as the monochromator, an X-ray beam can form a slit-to-slit image with a comparatively large angular field in the longitudinal direction of the slit, so that radiation from a comparatively large surface area of a specimen can be effectively measured, with the result that for a high resolution a high radiation efficiency can be achieved. A high resolution which is accompanied by a high radiation efficiency can be achieved notably by providing the apparatus with a curved entrance slit and a curved exit slit for the X-rays. The slits preferably follow respective circles of lattitude on the surface of a Rowland sphere having a radius R, namely circles formed by the intersection of the Rowland sphere with corresponding planes in transverse with respect the perpendicular to the crystal boundary surface erected at the center of the crystal boundary surface. When both slits are situated in the same plane, this plane is situated a distance $2R \sin 2\theta$ above the central point of the monochromator crystal which is also situated on the surface of the Rowland sphere. Therein, $\theta$ again represents the Bragg angle to be set up. Using this arrangement the ray aberrations are at least a factor 10 smaller than when use is made of a monochromator in the form of a Johansson crystal in combination with straight slits. Preferably, both slits have the same length which is at least substantially equal to a relevant transverse dimension of the monochromator crystal.

In a preferred embodiment, the boundary surface of a monochromator crystal whose crystal lattice surfaces have a radius of curvature 2R in all directions, exhibits a radius of curvature 2R in a first principal direction and a radius of curvature R in a principal direction transverse thereto, R being the radius of curvature of the Rowland sphere for the apparatus. The surface curvatures in the respective directions are graded progressively from one to the other to form a toroidal surface. The term toroidal is used herein in the optical sense to mean a smooth lens-like surface in which the curvature in one principal plane differs from that in a principal plane at right angles thereto.

In order to manufacture a monochromator crystal in accordance with the invention, a boundary surface of a monocrystal which is situated parallel to a parallel set of crystal lattice planes (planar surfaces), can be cylindrically recessed so as to be concave with, for example, a radius of curvature 2R, the crystal plate formed then being secured in a forming jig provided with a spherical forming surface which also has a radius of curvature 2R. The drawbacks involved in deforming a crystal plate of non-uniform thickness, can be avoided by first arranging a flat crystal plate in the spherical forming jig and then subsequently recessing the free boundary surface of the crystal in a toroidal manner. The drawback involved in making the recessing operation the last operation to be performed on the crystal, namely that undesirable stresses could remain in the crystal, can be avoided by cutting a cylindrical crystal plate from a monocrystal so that the plate has two coaxial cylindrical boundary surfaces and hence a uniform thickness, and subsequently deforming this crystal plate in a forming jig having a toroidal forming surface whose principal radii of curvature are R and 2R.

Some preferred embodiments in accordance with the invention will now be described in detail by way of example, with reference to the accompanying drawing.

The sole FIGURE of the drawing shows a diagrammatic view of a configuration in accordance with the invention and comprising a monochromator crystal, an entrance slit and an exit slit positioned with respect to a Rowland sphere.

The FIGURE shows a cross-section of a Rowland sphere having a radius R; this cross-section coincides with the plane of drawing and has a circumferential circle C and a center M. A first principal cross-section of the irradiated boundary surface of a monochromator crystal 1 whose diffracting crystal lattice surfaces are spherical with a (mean) radius of curvature 2R and which is mounted in a carrier 2, coincides with the plane of drawing. The direction of the tangent to the circle C at the central point O of the crystal will be referred to hereinafter as the x-direction. The upper boundary surface of the crystal, as shown in the drawing, thus has a radius of curvature R in this plane. A further principal cross-section of the upper boundary surface of the crystal in a direction perpendicular to the x-direction, referred to hereinafter as the y-direction, has a radius of curvature 2R, so that it does not coincide with the Rowland sphere in that direction. The z-direction is therefore the direction perpendicular to the x-y plane and the z-axis passes through the central point O of the crystal. The monochromator crystal is thus arranged in a Johansson configuration with respect to the x-z plane and in a Johann configuration with respect to the y-z plane.

A radiation entrance slit 3 and a radiation exit slit 4 are located at a distance h from O, measured along the z-axis. An x-ray tube 5 is arranged to irradiate a specimen 6. An X-ray beam thereform is formed about a main ray 7 through the central crystal point O by means of the entrance slit 3 and, after diffraction by the crystal 1, is intercepted by a detector 8 which is arranged beyond the exit slit 4. The exit slit 4 thus forms the radiation entrance slit for the detector.

For a diffraction angle $2\theta$ as shown in the FIGURE, the height h of the slits 3 and 4 for symmetrical reflection is given by $h=2R \sin^2 \theta$. This is applicable to a symmetrical position of the crystal for which the active crystal lattice surfaces at the center of the crystal extend parallel to the crystal boundary surface. By tilting the crystal about the y-axis, an asymmetrical arrangement can be provided whereby the heights of the entrance slit and the exit slit are made to differ.

By constructing the slits 3 and 4 so as to be curved, i.e. so that they form part of the Rowland sphere with a width direction with respect to the position of the crystal which coincides with a meridian and a length direction which coincides with a circle of lattitude of the Rowland sphere, optical aberrations in the imaging process are minimized. Preferably, the length of the slits is at least substantially equal to the diameter of the monochromator crystal. Using a diameter of 25 mm for the crystal, the length of the slits in a practical case also amounts to approximately 25 mm, their width being, for example, from 0.1 to 0.5 mm and the radius of the Rowland sphere being, for example, 150 mm. Thus, an arrangement is obtained in which X-ray fluorescence analysis can be performed on a specimen by displacing the slits, for example, in a linear spectrometer.

The monochromator crystal consists of, for example, silicon or germanium; these materials offer the advantage that large monocrystals can be formed therefrom in a comparatively simple manner and that plates of such a material can be deformed to a sufficiently large extent. In order to monochromatize longwave radiation, monocrystals can also be made of pentaerythritol, thallium hydrophtalate or other materials commonly used in X-ray fluorescence analysis.

Because only one of the two slits is effective in providing a high resolution while the other slit serves only as a radiation shield, one of the slits may be omitted. Use can also be made of an X-ray source having a curved, linear focus which can take the place of the entrance slit or of a detector having a correspondingly shaped effective entrance surface which in that case takes the place of the exit slit.

What is claimed is:

1. An X-ray analysis apparatus comprising an X-ray source, a doubly curved monochromator crystal having doubly curved crystal lattice surfaces, said monochromator crystal exhibiting mutually and significantly different amounts of surface curvature in different principal directions, and x-ray detector means for detecting X-rays from said monochromator crystal, wherein said first principal direction is transverse to said second principal direction.

2. An X-ray analysis apparatus comprising an X-ray source, a doubly curved monochromator crystal having doubly curved crystal lattice surfaces, said monochromator crystal exhibiting mutually and significantly different amounts of surface curvature in different principal directions, and x-ray detector means for detecting X-rays from said monochromator crystal, wherein said monochromator crystal is mounted at a Rowland sphere having a radius R, and wherein said monochromator crystal is curved in a first principal direction with said radius R and said monochromator crystal is curved in a second principal direction with a radius 2R.

3. An X-ray analysis apparatus according to claim 2, wherein said first principal direction is transverse to said second principal direction.

4. An X-ray analysis apparatus according to claim 1 or 2, wherein said doubly curved crystal lattice surfaces are spherically curved.

5. An X-ray analysis apparatus according to claim 4, wherein an entrance slit for passing X-rays from said X-ray source and an exit slit for passing said X-rays from said monochromator crystal to said detector means are provided on said Rowland sphere.

6. An X-ray analysis apparatus according to claim 5, wherein said entrance slit and said exit slit are both curved to coincide with a circle of latitude on said Rowland sphere relative to monochromator crystal, said circle of latitude defining a plane perpendicular to a perpendicular to a central point of said monochromator crystal.

7. An X-ray analysis apparatus according to claim 5, wherein incident and reflected X-rays on said monochromator crystal are inclined at an angle $\theta$ with respect to said spherically curved crystal lattice surfaces, and wherein said entrance slit and said exit slit are situated at a height along a perpendicular to a central point of said monochromator crystal where $h = 2R \sin^2 \theta$.

8. An X-ray analysis apparatus according to claim 5, wherein said entrance slit and said exit slit both have lengths at least substantially equal to a diameter of said monochromator crystal.

9. An X-ray analysis apparatus according to claim 4, wherein said X-ray source provides an adapted, curved, linear focus to serve as an entrance slit, and wherein said detector means has an entrance surface being an adapted, curved, active exit slit.

10. A monochromator crystal for an X-ray analysis apparatus comprising a doubly curved crystal having doubly curved crystal lattice surfaces, and said crystal exhibiting mutually and significantly different amounts of surface curvature in different directions, wherein said crystal is curved in a first principal direction with a radius R and said crystal is curved in a second principal direction with a radius 2R.

11. A monochromator crystal according to claim 10, wherein said first principal direction is transverse to said second principal direction.

12. A monochromator crystal for an X-ray analysis apparatus comprising a doubly curved crystal having doubly curved crystal lattice surfaces, and said crystal exhibiting mutually and significantly different amounts of surface curvature in different directions, wherein said crystal is curved in a toroidal shape having principal radii of curvature of R and 2R.

13. A monochromator crystal according to claim 10 or 12, wherein said crystal is one of silicon, germanium, pentaerythritol, and thallium hydrophtalate.

14. A method of manufacturing a monochromator crystal having mutually and significantly different amounts of surface curvature in different principal directions comprising the steps of
providing a cylindrical plate of material which exhibits X-ray diffraction,
arranging said plate in a forming jig, said forming jig having a toroidal forming surface with principal radii of curvature of R and 2R, and
deforming said plate in said forming jig to provide said principal radii of curvature R and 2R on the deformed plate.

* * * * *